United States Patent
Jann et al.

(10) Patent No.: US 7,091,194 B1
(45) Date of Patent: Aug. 15, 2006

(54) METHOD FOR INCREASING THE PRODUCTION OF PROPIONATE IN THE GASTROINTESTINAL TRACT

(75) Inventors: Alfred Jann, Publier (CH); Eva Arrigoni, Thalwil (CH); Florence Rochat, Montreux (CH); Daniel Schmid, Lausanne (CH); Anne Bauche, Lausanne (FR)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/979,533

(22) PCT Filed: May 19, 2000

(86) PCT No.: PCT/EP00/04744

§ 371 (c)(1),
(2), (4) Date: Mar. 8, 2002

(87) PCT Pub. No.: WO00/70964

PCT Pub. Date: Nov. 30, 2000

(30) Foreign Application Priority Data

May 20, 1999 (EP) .................................. 99109916

(51) Int. Cl.
*A61K 31/1721* (2006.01)
*A23L 1/054* (2006.01)
(52) U.S. Cl. .................... 514/59; 426/579; 426/548; 426/139; 426/310
(58) Field of Classification Search ........... 426/579, 426/548, 139, 310; 514/59
See application file for complete search history.

(56) References Cited

U.S. PATENT DOCUMENTS

| | | | | | |
|---|---|---|---|---|---|
| 2,731,349 | A | * | 1/1956 | Toulmin | 426/139 |
| 2,790,720 | A | * | 4/1957 | Novak | 426/310 |
| 2,893,873 | A | * | 7/1959 | Novak | 426/548 |
| 2,938,799 | A | * | 5/1960 | Toulmin | 426/579 |

FOREIGN PATENT DOCUMENTS

| | | |
|---|---|---|
| EP | 0 153 013 A2 | 8/1985 |
| EP | 0 382 355 A2 | 8/1990 |
| EP | 0 881 283 A1 | 12/1998 |
| JP | 60-190717 | 9/1985 |

OTHER PUBLICATIONS

"Pharmaceutical Aspects of Dietary Fibre" by Professor N.W. Read.
"Dietary Fructans", Roberfroid et al., *Annu. Rev. Nutr.*, 1998, vol. 18, pp. 117-143.
"Dietary Fructans", Roberfroid et al., *Annu. Rev. Nutr.*, 1998, vol. 18, pp. 117-143.

* cited by examiner

*Primary Examiner*—Irene Marx
(74) *Attorney, Agent, or Firm*—Bell, Boyd & Lloyd LLC

(57) ABSTRACT

A method for selectively increasing the production of propionate in the gastro-intestinal tract of a mammal. The method includes the step of enterally administering to the mammal a nutritional composition which contains dextran. Increasing the propionate production results in decreased blood cholesterol levels, decreased blood triglyceride levels, decreased very low density lipoprotein levels, increased high density lipoprotein levels, and increased insulin sensitivity.

3 Claims, No Drawings

METHOD FOR INCREASING THE PRODUCTION OF PROPIONATE IN THE GASTROINTESTINAL TRACT

FIELD OF THE INVENTION

This invention relates to a method for preferentially increasing the synthesis of propionate in the gastrointestinal tract by administering dextran. The invention also relates to methods for the nutritional management of blood cholesterol levels, blood triglyceride levels, blood lipoprotein levels, and insulin sensitivity by administering dextran.

BACKGROUND TO THE INVENTION

Certain non-digestible polysaccharides, which are often termed prebiotic fibres, are fermented by micro-organisms in the gastrointestinal tract. Examples of these polysaccharides are inulin and its hydrolysis products. The products of the fermentation lead to the provision of energy, the selective stimulation of growth of lactic acid bacteria and the regulation of cellular metabolism. One class of these fermentation products are the short chain fatty acids acetate, propionate and butyrate.

Of the short chain fatty acids, propionate is thought to (i) mediate the reduced hepatic gluconeogenesis induced by non-digestible polysaccharides, (ii) inhibit gluconeogenesis in the liver, (iii) enhance glycolysis, (iv) lower plasma fatty acid concentrations, (v) inhibit ureagenesis in the liver, and (v) increase insulin sensitivity (Roberfroid et al; 1998; *Annu. Rev. Nutr.*; 18:117–43). Acetate, however, increases plasma fatty acid concentrations (Roberfroid et al; 1998; *Annu. Rev. Nutr.*; 18:117–43).

The selective production of propionate in the gastrointestinal tract would therefore be of benefit in the nutritional management of many conditions. However, the primary fatty acid which is produced upon fermentation of known non-digestible polysaccharides is acetate, followed by butyrate and propionate. Hence these non-digestible polysaccharides are not suitable for selectively increasing the production of propionate in the gastrointestinal tract.

Therefore, it is an object of this invention to provide a method for selectively increasing the production of propionate in the gastro-intestinal tract.

SUMMARY OF THE INVENTION

Accordingly, in one aspect, this invention provides a method for selectively increasing the production of propionate in the gastrointestinal tract, the method comprising enterally administering to a mammal a nutritional composition which contains dextran.

It has been surprisingly found that dextran, when fermented by micro-organisms which occur in the gastrointestinal tract, results in the increased production of propionate when compared to other non-digestible polysaccharides. Therefore, dextran is an ideal source of propionate in the gastro-intestinal tract.

The term "dextran" means a group of polysaccharide which are composed of α-D-glucopyranosyl units linked predominantly α-D(1→6). Dextrans are produced by certain types bacteria growing on a glucose substrate; for example *Leuconostoc mesenteroides*, *Leuconostoc dextranicum*, and *Leuconostoc mesenteroides* ssp. *cremoris*. Further, shorter chain dextrans may be obtained by hydrolysing native dextrans or by synthesising them.

In another aspect, this invention provides a method for decreasing blood cholesterol levels in a mammal, the method comprising enterally administering to a mammal a nutritional composition which contains dextran.

In another aspect, this invention provides a method for decreasing blood triglyceride levels in a mammal, the method comprising enterally administering to a mammal a nutritional composition which contains dextran.

In another aspect, this invention provides a method for decreasing very low density lipoprotein levels in a mammal, the method comprising enterally administering to a mammal a nutritional composition which contains dextran.

In another aspect, this invention provides a method for increasing high density lipoprotein levels in a mammal, the method comprising enterally administering to a mammal a nutritional composition which contains dextran.

In another aspect, this invention provides a method for increasing insulin sensitivity in a mammal, the method comprising enterally administering to a mammal a nutritional composition which contains dextran.

DETAILED DESCRIPTION OF THE PREFERRED EMBODIMENTS

Embodiments of the invention are now described, by way of example only.

This invention is based upon the discovery that the colonic fermentation of dextran by micro-organisms results in the production of relatively larger amounts of propionate as compared to other non-digestible polysaccharides. Therefore, the enteral administration of dextran provides a convenient and simple way of selectively increasing the production of propionate in the gastro-intestinal tract.

The dextran used may be any suitable dextran; natural, synthetic or partially hydrolysed. Suitable dextrans are commercially available or may be produced by growing *Leuconostoc* micro-organisms on a sucrose substrate and isolating and purifying the dextran. Alternatively, the dextran may be produced as described in European patent application 0881283.

Preferably, however, the dextran is a high molecular weight dextran; for example having a molecular weight above 50000, preferably above about 70000, more preferably above about 100000; for example above about 500000.

The dextran may be formulated into any suitable nutritional composition as desired since the exact composition and form is not critical. One suitable class of nutritional compositions is food products. Examples of suitable food products include yoghurts, ice cream confections, milk-based drinks, salad dressings, sauces, toppings, desserts, confectionery products, biscuits, cereal-based snack bars, prepared dishes, and the like. For humans, food products which are convenience foods are preferred since patient compliance is increased. Another suitable class of nutritional compositions is nutritional formulas such as enteral formulas for clinical and infant nutrition, and nutritional supplements. For pets, the nutritional compositions may be in the form of pet foods such as dried kibbles and retorted wet products.

The nutritional compositions may contain other ingredients as desired. For example, the nutritional compositions may contain other polysaccharides such as insoluble and soluble fibres. Fibres are known to have a beneficial effect upon cholesterol and glucose levels. Suitable sources of soluble and insoluble fibres are commercially available.

An example of a suitable fibre is inulin or its hydrolysis products. The inulin may be provided in the form of a natural extract which is suitable for human consumption. Suitable inulin extracts may be obtained from Oraffi SA of Tirlemont 3300, Belgium under the trade mark "Raftiline". For example, the inulin may be provided in the form of Raftiline®ST which is a fine white powder which contains about 90 to about 94% by weight of inulin, up to about 4% by weight of glucose and fructose, and about 4 to 9% by weight of sucrose. The average degree of polymerisation of the inulin is about 10 to about 12. The hydrolysis products of inulin are fructo-oligosaccharides in the form of fructose oligomers containing 1-kestose(GF2), nystose(GF3), and 1F-fructofuranosyl nystose(GF4), in which fructosyl units (F) are bound at the β-2,1 position of sucrose(GF) respectively. The fructo-oligosaccharides may be obtained commercially, for example from Orafti SA of Tirlemont 3300, Belgium under the trade mark "Raftilose", or from Meiji Seika Co. of Japan. For example, the fructo-oligosaccharides may be provided in the form of Raftilose®P95. Other oligosaccharides may be included if desired. Suitable examples are galacto-oligosaccharides, xylo-oligosaccharides or oligo derivatives of starch.

If both soluble and insoluble fibre are used, the ratio of soluble fibre to insoluble fibre is preferably about 1:3 to about 3:1; more preferably about 1:1 to about 2:1.

The nutritional composition may also contain vitamins and minerals as desired. For clinical applications, the nutritional composition preferably includes a complete vitamin and mineral profile. For example, sufficient vitamins and minerals may be provided to supply about 25% to about 250% of the recommended daily allowance of the vitamins and minerals per 1000 calories of the nutritional composition.

When the nutritional composition is in the form of a food product or nutritional formula, the nutritional composition may contain a protein source, a lipid source and a carbohydrate source. These sources may be selected as desired.

The lipid source is preferably rich in monounsaturated fatty acids; for example monounsaturated fatty acids may provide at least 50% of energy of the lipid source. The lipid source may also contain polyunsaturated fatty acids (omega-3 and omega-6 fatty acids). The lipid profile is preferably designed to have a polyunsaturated fatty acid omega-6 (n-6) to omega-3 (n-3) ratio of about 4:1 to about 10:1. Saturated fatty acids preferably provide less than 20% of the energy of the lipid source; for example less than about 15%.

The nutritional composition may be used in the nutritional management of conditions such as diabetes and hypercholesterolemia.

The amount of the nutritional composition required to be fed to a patient will vary depending upon factors such as the patient's condition, the patient's body weight, the age of the patient, and whether the nutritional composition is the sole source of nutrition. However the required amount may be readily set by a medical practitioner. In general, sufficient of the nutritional composition is administered to provide the patient with up to about 40 g of dietary fibre (insoluble and soluble) per day; for example about 25 g to about 35 g of dietary fibre per day. The amount of dextran that the patient receives is preferably in the range of about 2 g to about 15 g per day. If the nutritional formula is used as a supplement to other foods, the amount of the nutritional composition that is administered daily may be decreased accordingly.

The nutritional composition may be taken in multiple doses, for example 2 to 5 times, to make up the required daily amount or may taken in a single dose. The nutritional composition may also be fed continuously over a desired period.

The invention is now further described with reference to the following specific examples.

EXAMPLE 1

Three non-digestible polysaccharides are fermented in an in vitro fermentation model which simulates fermentation conditions in the gastro-intestinal tract. The polysaccharides are (i) acacia gum (available under the trade name Fibregum), (ii) Dextran produced according to European patent application 0881283, and (iii) lactulose.

For each polysaccharide, an amount of 100 mg of the polysaccharide is added to 8 ml of a carbonate-phosphate buffer, which contains oligo-elements, in a 50 ml air-tight flask. The composition of the buffer is as follows:—

| Component | Amount |
| --- | --- |
| $NaHCO_3$ | 9.240 g/l |
| $Na_2HPO_4.12H_2O$ | 7.125 g/l |
| NaCl | 0.470 g/l |
| KCl | 0.450 g/l |
| Urea | 0.400 g/l |
| $CaCl_2.6H_2O$ | 0.108 g/l |
| $Na_2SO_4$ | 0.100 g/l |
| $MgCl_2.6H_2O$ | 0.100 g/l |
| $FeSO_4.7H_2O$ | 36.80 mg/l |
| $MnSO_4.H_2O$ | 11.59 mg/l |
| $ZnSO_4.7H_2O$ | 4.40 mg/l |
| $CoCl_2.6H_2O$ | 1.20 mg/l |
| $NiCl_2$ | 1.00 mg/l |
| $CuSO_4.5H_2O$ | 0.98 mg/l |
| $Mo_7(NH_4)_6O_{24}.4H_2O$ | 0.17 mg/l |
| Resazurine | 1.00 mg/l |

Each flask is rinced for 1 minute with $CO_2$ gas and stored at 4° C. for 16 hours under a slight over-pressure.

Dilute human faeces is prepared from samples of fresh faeces collected from healthy humans not having consumed antibiotics for at least 3 months and not producing methane. The faeces are immediately rinced with $CO_2$ gas, and 3 parts (weight/weight) of the carbonate-phosphate buffer with oligo-elements are rapidly added at 37° C. The mixture is blended for 2 minutes in a stomacher (Stomacher 400, Seward, London, GB) and filtered by a Polymon PES1000/45 filter with 1 mm holes (Schweizerische Seidenfabrik SA, Zürich, CH).

An amount of 2 ml of the dilute faeces is added to each flask and the head space gas is replaced by a flux of temperate $CO_2$ gas for 1 minute. After equilibration of the pressure, each flask is sealed air-tight and incubated in an agitated water bath at 37° C.

After 24 hours, the content of short chain fatty acids in the flasks determined twice by direct injection of an acidified and sterile filtered sample on a gas chromatograph with FID (HP 8960, Hewlett Packard, Urdorf, CH) fitted with a DB-FFAP capillary column (MSP FRIEDLI & Co, Koeniz, CH). The results are as follows:—

| Polysaccharide | Short Chain fatty acid | SCFA Content (μmol/100 mg) | SCFA % of total* |
| --- | --- | --- | --- |
| Fibregum | Acetate | 648.2 | 63.7 |
| | Propionate | 228.6 | 22.5 |
| | Butyrate | 107.1 | 10.5 |
| Dextran | Acetate | 415.0 | 46.3 |
| | Propionate | 363.5 | 40.6 |
| | Butyrate | 87.6 | 9.8 |

-continued

| Polysaccharide | Short Chain fatty acid | SCFA Content (µmol/100 mg) | SCFA % of total* |
|---|---|---|---|
| Lactulose | Acetate | 909.2 | 74.6 |
|  | Propionate | 111.7 | 9.2 |
|  | Butyrate | 172.2 | 14.1 |

*the percentages do not added up to 100% since other short chain fatty acids are present in minor amounts.

The results indicate that fermentation of dextran results in increased production of propionate; relatively and absolutely. For the other polysaccharides, only acetate was favoured.

EXAMPLE 2

A study is undertaken with 45 mice aged between 7 and 10 weeks. The mice are kept in sterile conditions in cages. The mice have free access to water and a standard diet.

On the first day of the study, each mouse is fed 0.5 ml of a complete human microbial flora, diluted 100 times, by intra-gastric tube. The feeding is repeated on day 2. On day 11, the mice are separated into three groups; each group being housed in a separate sterile isolation unit.

On day 15, each group of mice receives a test diet. The test diets are sterile. The test diets all contain a potato puree, sugar, fish meal, cellulose, vitamins and minerals and a non-digestible polysaccharide. The polysaccharides are as follows:—

| Diet | Polysaccharide |
|---|---|
| Positive Control | Fructo-oligosaccharide (Raftilose) |
| Negative Control | Cellulose |
| Diet 1 | Dextran |

The mice are fed the diets until day 36. During this time, the development of the intestinal flora of each mouse is monitored by collecting faeces and determining microbial counts. A blood sample is collected from each mouse and analysed for short chain fatty acids. The mice are then anaesthetised and sacrificed. The caecum and stomach contents of each mouse is removed and analysed for short chain fatty acids and microbial flora, respectively.

All mice fed Diet 1 have relatively higher levels of propionate in the blood and caecum.

EXAMPLE 3

A study was performed to evaluate with 3 to 5 volunteers whether a significant increase of propionic acid could be meausred in feces after consumption of an acute dose of 15 g Dextran T2000 and a chronic dose of 10 g Dextran T2000 per day.

This study was performed as a randomiszed placebo-controlled double blind study with 4 volunteers in a cross-over design. SCFAs were measured in feces. Additionally, blood formula and selected blood proteins were measured before and after consumption of the dextran.

Outline of Results
  a) the effect of an accute dose of 15 g dextran on propionic acid in feces was investigated. The pool of feces collected between 12 and 72 hours after consumption of the acute does was analysed for short chain fatty acids (SCFAs). Taking the average results of the 4 volunteers, propionic acid infeces of the pool increased by 3.43 mmol in the treatmetn group relative to the placebo group.
  b) a chronic consumption of 10 g dextran per day was investigated. Propionic caid concentration in a fecal sample was analysed after 1 week of chronic consumption. Taking the average of the 4 volunteers, propionic acid concentration increased by 24.0 µmol/g dry feces in the treatment group compared to a decrease of 5.7 lmol/g dry feces in the placebo group.

Consumption of dextran induced no relevant changes of blood formula, investigated blood proteins or blood plasma enzymes. No clinical symptoms have been reported.

Conclusions

The results indicate an increase in the level of propionic acid in the gastro-intestinal tract following consumption of dextran.

Results

A summary of results from the study on dextran is set out below. This was a placebo controlled double blind study with a cross-over design. 4 volunteers were enrolled.

Results are given separately for treatment (Dextran) and placebo (maltodextrin). Additionally results relative to placebo are given.

| fecal samples (1 week intake of 10 g per day) | | | | C2: acetic acid C3: propionic acid | |
|---|---|---|---|---|---|
| volunteer | pionate conc. | C3/C2 | % propionic acid | In average: | |
| Treatment | | | | | |
| 1 | 89.89 | −0.139 | 0.1 | | |
| 2 | −13.73 | −0.087 | −2.7 | | |
| 3 | 1.31 | 0.071 | 6.8 | During treatment, propionate concentration increased by 24.0 µmol/g dry feces. | |
| 4 | 18.43 | 0.007 | 3.3 | During treatment, propionate/acetate ratio decreased by 0.04. | |
| av | 23.98 µmol/g dry | −0.037 | 1.9 | During treatment, % age of propionate on total SCFAs increased by 1.9%. | |
| Placebo | | | | | |
| 1 | 11.39 | −0.027 | −0.7 | | |
| 2 | −2.35 | −0.144 | −4.6 | | |
| 3 | −27.51 | −0.041 | −0.9 | During placebo, propionate concentration decreased by 5.7 µmol/g dry feces. | |
| 4 | −4.36 | −0.002 | −0.2 | During placebo, propionate/acetate ratio decreased by 0.05. | |
| av | −5.71 µmol/g dry | −0.054 | −1.6 | During placebo, % age of propionate on total SCFAs decreased by 1.6%. | |

-continued

| fecal samples (1 week intake of 10 g per day) | | | | C2: acetic acid |
| --- | --- | --- | --- | --- |
| | | | | C3: propionic acid |
| volunteer | pionate conc. | C3/C2 | % propionic acid | In average: | treatm − plac.

| | | | | |
| --- | --- | --- | --- | --- |
| 1 | 78.50 | −0.112 | 0.8 | |
| 2 | −11.38 | 0.057 | 1.9 | |
| 3 | 28.82 | 0.112 | 7.7 | Relative to placebo, propionate concentration increased by 29.7 μmol/g dry feces. |
| 4 | 22.79 | 0.009 | 3.5 | Relative to placebo, propionate/acetate ration increased by 0.02. |
| av | 29.68 μmol/g dr | 0.02 | 3.5 | Relative to placebo, % age of propionate on total SCFAs increased by 3.5%. |

| p ol of feces (12h to 72h after intake of 15 g) | | | | In blood, no changes in SCFA concentrations were observed. |
| --- | --- | --- | --- | --- |
| C3 produce | C3 in tot | C3/C2 | conc. C3 (μmol/g wet) | In average: | treatment

| | | | | |
| --- | --- | --- | --- | --- |
| 1 | 29.65 | 30.32 | 0.57 | 35.54 | |
| 2 | 2.26 | 20.98 | 0.39 | 8.61 | During treatment, propionate production was 10.8 mmol. |
| 3 | 8.41 | 22.31 | 0.47 | 35.86 | During treatment, % age of propionate on total SCFAs was 23%. |
| 4 | 2.91 | 18.20 | 0.34 | 13.88 | During treatment, propionate by acetate ratio 0.44. |
| av | 10.81 | 22.95 | 0.44 | 23.47 | During treatment, propionate concentration was 23.5 μmol/g wet feces. | placebo

| | | | | |
| --- | --- | --- | --- | --- |
| 1 | 17.11 | 24.84 | 0.44 | 26.84 | |
| 2 | 3.91 | 18.13 | 0.35 | 11.97 | During treatment, propionate production was 7.4 mmol. |
| 3 | 4.46 | 22.37 | 0.48 | 22.96 | During treatment, % age of propionate on total SCFAs was 20.4%. |
| 4 | 4.04 | 16.39 | 0.27 | 10.35 | During treatment, propionate by acetate ratio 0.39. |
| av | 7.38 | 20.43 | 0.39 | 18.03 | During treatment, propionate concentration was 18.0 μmol/g wet feces. | treatment − placebo

| | | | | |
| --- | --- | --- | --- | --- |
| 1 | 12.54 | 5.48 | 0.13 | 8.69 | |
| 2 | −1.65 | 2.84 | 0.04 | −3.37 | Relative to placebo, propionate production was 3.4 mmol. |
| 3 | 3.95 | −0.06 | −0.01 | 12.90 | Relative to placebo, % age of propionate on total SCFAs was 2.5%. |
| 4 | −1.12 | 1.81 | 0.06 | 3.53 | Relative to placebo, propionate/acetate ration increased by 0.06 (or 15%). |
| av | 3.43 | 2.52 | 0.06 (=+15%) | 5.44 | Relative to placebo, propionate concentration increased by 5.4 μmol/g wet feces. |

The invention claimed is:

1. A method for increasing production of propionate in a gastro-intestinal tract of a mammal by orally administering a nutritional composition comprising dextran having a molecular weight of about 2,000,000 wherein dextran is administered in an amount from about 10 g per day to about 15 g per day.

2. The method according to claim 1 wherein the nutritional composition further comprises at least one component selected from the group consisting of inulin, fructo-oligosaccharide, galacto-oligosaccharides, xylo-oligosaccharides, and a mixture thereof.

3. The method according to claim 1 wherein the nutritional composition further comprises a lipid source that includes a monounsaturated fatty acid and a saturated fatty acid and wherein the monounsaturated fatty acid provides at least 50% of energy of the lipid source and the saturated fatty acid provides less than 20% of energy of the lipid source.

* * * * *